(12) United States Patent
Pigeau et al.

(10) Patent No.: US 8,759,049 B2
(45) Date of Patent: Jun. 24, 2014

(54) METHOD FOR THE PRODUCTION OF A FERMENTATION PRODUCT FROM A SUGAR HYDROLYSATE

(75) Inventors: Gary M. Pigeau, Ontario (CA); Jan-Maarten A. Geertman, Voorschoten (NL)

(73) Assignee: Iogen Energy Corporation, Ontario (CA)

( * ) Notice: Subject to any disclaimer, the term of this patent is extended or adjusted under 35 U.S.C. 154(b) by 407 days.

(21) Appl. No.: 13/032,127

(22) Filed: Feb. 22, 2011

(65) Prior Publication Data

US 2011/0207192 A1 Aug. 25, 2011

Related U.S. Application Data

(60) Provisional application No. 61/308,028, filed on Feb. 25, 2010.

(51) Int. Cl.
*C12P 1/02* (2006.01)
*C12P 7/06* (2006.01)
*C12P 7/14* (2006.01)
*C12P 7/10* (2006.01)

(52) U.S. Cl.
USPC ............ 435/161; 435/162; 435/165; 435/171

(58) Field of Classification Search
None
See application file for complete search history.

(56) References Cited

U.S. PATENT DOCUMENTS

| | | | |
|---|---|---|---|
| 4,929,365 A | 5/1990 | Clark et al. | |
| 6,840,251 B2 | 1/2005 | Gill et al. | |
| 8,192,968 B2 * | 6/2012 | Edwards et al. | 435/158 |
| 2003/0190742 A1 | 10/2003 | Whiteman | |
| 2009/0117663 A1 | 5/2009 | Sharping et al. | |
| 2009/0251762 A1 | 10/2009 | Lenssen et al. | |

FOREIGN PATENT DOCUMENTS

| | | |
|---|---|---|
| WO | 2004072291 | 8/2004 |
| WO | 2007097874 | 8/2007 |
| WO | 2007149450 | 12/2007 |
| WO | 2009026706 | 3/2009 |

OTHER PUBLICATIONS

Benarde et al., "Kinetics and Mechanism of Bacterial Disinfection by Chlorine Dioxide", Applied Microbiology, vol. 15, No. 2 (1967) 257-65.

Bernarde et al., "Chlorine Dioxide Disinfection Temperature Effects", J. Appl. Bact., vol. 30, No. 1 (1967) 159-67.

Chandranupap, et al., "Effect of pH on kinetics and bleaching efficiency of chlorine dioxide delignification", Applta Journal, vol. 53, No. 2 (2000) 108-10.

(Continued)

*Primary Examiner* — Rebecca Prouty
(74) *Attorney, Agent, or Firm* — Fitzpatrick, Cella, Harper & Scinto

(57) ABSTRACT

The present invention relates to a method for producing a fermentation product from a sugar hydrolysate. The method comprises fermenting the sugar hydrolysate in a fermentation system with yeast to produce a fermentation broth comprising a fermentation product; introducing acid and an oxidant, such as chlorine dioxide, to the fermentation system so as to expose microbial contaminants in the fermentation system at one or more stages to chlorine dioxide and a pH of less than 3.0; and recovering the fermentation product. In one example of the invention, a yeast slurry obtained from a yeast recycle step is treated with acid and the oxidant.

24 Claims, 6 Drawing Sheets

(56) References Cited

OTHER PUBLICATIONS

Chang et al., "Use of Sulfite and Hydrogen Peroxide to Control Bacterial Contamination in Ethanol Fermentation", Appl. Environ. Microbiol., vol. 63, No. 1 (1997) 1-6.

"Chlorine dioxide in the beverage industry", Petplanet Insider, vol. 6 (2005) 46-7.

Dence, et al., "Pulp Bleaching, Principles and Practice", Chapter 3: Chlorine Dioxide in Delignification in Pulp Bleaching, Tappi Press (1996) 276-79.

de Oliva-Neto, et al., "Susceptibility of *Saccharomyces cerevisiae* and Lactic Acid Bacteria From The Alcohol Industry to Several Antimicrobial Compounds", Brazilian Journal of Microbiology, vol. 32 (2001) 10-4.

"Alternative Disinfectants and Oxidants Guidance Manual", United States Environmental Protection Agency, (1999) Chapter 4, Chlorine Dioxide, 1-41.

Foegeding et al., "Chlorine Dioxide Inactivation of *Bacillus* and *Clostridium* Spores", Journal of Food Science, vol. 51, No. 1 (1986)197-201.

Han et al., "Efficacy of chlorine dioxide gas as a sanitizer for tanks used for aseptic juice storage", Food Microbiology, vol. 16 (1999) 53-61.

Hoigne, et al., "Kinetics of Reactions of Chlorine Dioxide (OCIO) in Water—I. Rate Constants for Inorganic and Organic Compounds", Water Res., vol. 28, No. 1 (1994) 45-55.

Johnson, et al., "Coming Clean—A New Method of Washing Yeast Using Chlorine Dioxide", The New Brewer, vol. 15 (1998) 1-6.

Kim, et al., "Production and stability of chlorine dioxide in organic acid solutions as affected by pH, type of acid, and concentration of sodium chlorite, and its effectiveness in inactivating *Bacillus cereus* spores", Food Microbiology, vol. 25 (2008) 964-69.

Kolar et al., "Chemical Reactions in Chlorine Dioxide Stages of Pulp Bleaching", Wood Sci. Technology, vol. 17 (1983) 117-28.

Lushia, et al., "Antibiotic-Resistant Bacteria in Fuel Ethanol Fermentations", Ethanol Producer (2005).

Ramirez-Orozco et al., "*Debaryomyces hansenii* growth in nonsterile seawater ClO2—peptone-containing medium", Can. J. Microbiol., vol. 47 (2001) 676-79.

Rapson, "Bleaching-Chlorine Dioxide", Handbook of Pulp and Paper Technology, Reinhold Company, Chapter 4-4 (1970) 275-86.

Svenson et al., "Effect of pH on the Inorganic Species Involved in a Chlorine Dioxide Reaction System", Ind. Chem. Res., vol. 41 (2002) 5927-33.

* cited by examiner

METHOD FOR THE PRODUCTION OF A FERMENTATION PRODUCT FROM A SUGAR HYDROLYSATE

CROSS-REFERENCE TO RELATED APPLICATIONS

This application claims the priority benefit of a provisional application No. 61/308,028, filed Feb. 25, 2010, which is incorporated herein by reference.

FIELD OF INVENTION

The present invention relates to a method for the production of a fermentation product. More specifically, the present invention relates to a method for the production of a fermentation product from a sugar hydrolysate.

BACKGROUND OF THE INVENTION

Lignocellulosic feedstock is a term commonly used to describe plant-derived biomass comprising cellulose, hemicellulose and lignin. Much attention and effort has been applied in recent years to the production of fuels and chemicals, primarily ethanol, from lignocellulosic feedstocks, such as agricultural wastes and forestry wastes, due to their low cost and wide availability. These agricultural and forestry wastes are typically burned or land-filled; thus using these lignocellulosic feedstocks for ethanol production offers an attractive alternative to disposal. Yet another advantage of these feedstocks is that the lignin byproduct, which remains after the cellulose conversion process, can be used as a fuel to power the process instead of fossil fuels. Several studies have concluded that, when the entire production and consumption cycle is taken into account, the production of ethanol from lignocellulosic feedstocks generates close to zero greenhouse gases.

The first chemical processing step for converting lignocellulosic feedstock to ethanol, or other fermentation products, involves breaking down the fibrous lignocellulosic material to liberate sugar monomers from the feedstock for conversion to a fermentation product in a subsequent step of fermentation.

There are various known methods for producing fermentable sugars from lignocellulosic feedstocks, one of which involves an acid or alkali pretreatment followed by hydrolysis of cellulose with cellulase enzymes and β-glucosidase. The purpose of the pretreatment is to increase the cellulose surface area and convert the fibrous feedstock to a muddy texture, with limited conversion of the cellulose to glucose. Acid pretreatment typically hydrolyses the hemicellulose component of the feedstock to yield xylose, glucose, galactose, mannose and arabinose and this is thought to improve the accessibility of the cellulose to cellulase enzymes. The cellulase enzymes hydrolyse cellulose to cellobiose which is then hydrolysed to glucose by beta-glucosidase. Hydrolysis of the cellulose and hemicellulose can also be achieved with a single-step chemical treatment in which the lignocellulosic feedstock is contacted with a strong acid or alkali under conditions sufficient to hydrolyse both the cellulose and hemicellulose components of the feedstock to sugar monomers.

After production of a stream comprising fermentable sugar from the lignocellulosic feedstock, a solids separation may be conducted to remove lignin, followed by fermentation of the sugars to ethanol or other fermentation products. If glucose is the predominant substrate present, the fermentation is typically carried out with a *Saccharomyces* spp. yeast that converts this sugar and other hexose sugars present to ethanol. However, glucose can also be fermented to other commercial products including lactic acid, sorbitol, acetic acid, citric acid, ascorbic acid, propanediol, butanediol, xylitol, acetone, and butanol. This conversion can be carried out by a variety of organisms, including *Saccharomyces* spp.

The pentose sugars, xylose and arabinose, which arise from the hemicellulose component of the feedstock during acidic pretreatment, can be fermented to ethanol. However, a vast majority of wild-type *Saccharomyces* strains do not naturally contain all the genes required for converting these sugars to ethanol. Thus they must be introduced into the yeast to allow for this conversion. Recombinant yeasts that are able to convert xylose to ethanol are described, for example, in U.S. Pat. Nos. 5,789,210 and 6,475,768 and EP 1 727 890.

One problem with the fermentation of sugar to ethanol or other fermentation products is that bacteria can propagate quickly as the optimum conditions of the fermentation are also conducive to their growth. Unwanted byproducts that can be produced by bacterial contaminants during fermentation include lactic acid, acetone and propionic acid. Lactic acid is a common byproduct produced by bacteria such as *Lactobacillus* spp, *Pediococcus* spp, *Leuconostoc* spp and/or *Weissella* spp (amongst others) during ethanol fermentations. The production of such undesirable byproducts decreases the yield of the desired fermentation product as the bacteria compete with the yeast for fermentable sugars and convert them to undesirable byproducts instead of the fermentation product of interest. Moreover, organic acids and other byproducts can be inhibitory to the yeast. Each of these factors can contribute to decreases in the efficiency of the fermentation by lengthening the time required for carrying out the fermentation, increasing the amount of yeast required and/or decreasing the final yields to the desired fermentation product from the fermentable sugars.

Microbial contamination is especially problematic when the concentration of yeast in the fermentor is increased by yeast recycle. Yeast recycle is employed to improve the efficiency of fermentation processes that are subject to slow reaction kinetics relative to glucose fermentation such as those involving the conversion of xylose to ethanol or when it is beneficial to increase volumetric conversion rates. Increases in the volumetric rate of conversion of fermentable sugar to ethanol can be achieved by continuously separating yeast from the harvested fermentation broth, such as by centrifugation, and then re-circulating the yeast back to the fermentor. By re-introducing yeast into the reactor in this manner, the concentration of yeast in the fermentor is continuously maintained at a high level, without significant diversion of sugars to cell growth and away from the desired fermentation product. However, as a result of such repeated re-circulation of yeast, unwanted microbes, such as bacteria, are also recycled along with the yeast. As bacteria tend to divide more quickly than yeast, this can lead to significant levels of microbial contamination.

de Oliva-Neto and Yokoya (Brazilian Journal of Microbiology, 2001, 3:10-14) examined the effect of a variety of antimicrobial compounds on the viability of *Saccharomyces cerevisiae, Lactobacillus* and *Leuconostoc* in fermentations carried out on cane juice to produce ethanol. This included formulated chemicals, such as zinc manganese ethylenebis (dithiocarbamate), methyldithiocarbamate, 3-methyl-4-chlorophenol, 2-benzyl-4-chlorophenol and o-phenylphenol, 2-chloroacetamide and others, that are commonly recommended for use in microbial control in sugar and alcohol factories. Antibiotics tested included penicillum, clindamycin and cephamandole. The results showed that current chemical biocides used in industrial fuel alcoholic fermentations reduced yeast viability, while antibiotics were effective at reducing bacterial growth, without affecting yeast viability.

However, the use of antibiotics in fuel ethanol applications has its limitations as microbial contaminants are known to develop antibiotic resistance (Lushia and Heist, 2005, Ethanol Producer Magazine, Antibiotic-Resistant Bacteria in Fuel Ethanol Fermentations). Moreover, antibiotics can be carried through to dried distillers grain, which is a byproduct of commercial ethanol plants used in animal feeds, and this valuable byproduct cannot be sold if antibiotics are used in the process.

Bacterial control in industrial fuel alcoholic fermentation can also be carried out by sulfuric acid washing of yeast cell suspensions. Commercial fuel ethanol in Brazil is produced by fed-batch or continuous fermentation of sugar cane by *Saccharomyces cerevisiae* and employs yeast cell recycle (de Oliva-Neto and Yokoya, supra). The goal of the acid treatment is to destroy contaminating microorganisms that cannot withstand low pH conditions, without a substantial reduction in yeast viability or fermentative capacity.

US2009/0117633 discloses a process for producing ethanol from corn in which a combined saccharification and fermentation are conducted at pH values such as 3.5 to 4.0. The enzymes used in the saccharification are amylases that are adapted for hydrolysing starch under these relatively low pH values. The low pH saccharification/fermentation is conducted with the view of reducing bacterial contaminants such as lactic acid-producing and acetic acid-producing bacteria, which grow best at pH 5.0 and above. Thus, in the pH range of 3.0 to 4.5, it is believed that ethanol fermentation will predominate because yeast will grow better than contaminating bacteria.

The use of oxidants to control microbial contamination in ethanol fermentations is also known. For example, Chang et al. (Appl. Environ. Microbiol., 1997, 63: 1-6) disclose the use of sulfite and hydrogen peroxide to control bacterial contamination in the fermentation of malt extract to ethanol with yeast recycle.

Chlorine dioxide is an oxidant that is known to have a bacteriocidal effect and has been used as a disinfectant of drinking water and in the food and beverage industry. There are various known methods for producing chlorine dioxide, (see Alternative Disinfectants and Oxidants Guidance Manual, United States Environmental Protection Agency, April 1999, Chapter 4. Chlorine Dioxide, which is incorporated herein by reference) one of which involves reacting sodium chlorite with acid according to the following reaction:

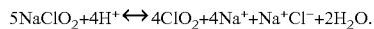
$$5NaClO_2 + 4H^+ \leftrightarrow 4ClO_2 + 4Na^+ + Na^+Cl^- + 2H_2O.$$

Sodium chlorite is often referred to as "stabilized chlorine dioxide" or "SCD".

The use of chlorine dioxide in ethanol fermentations is known as set forth in WO 2007/097874, WO 2009/026706, WO 2007/149450 and Johnson and Kunz (The New Brewer, 1998, Coming Clean—A New Method of Washing Yeast Using Chlorine Dioxide Vol. 15 #5-P56). WO 2007/097874 discloses a process in which chlorine dioxide is added to a fermentation tank, to a fermentable carbohydrate added to a fermentation tank, or to a propagation or conditioning system used to prepare the inoculum for a fermentation. WO 2009/026706 discloses the use of chlorine dioxide to reduce bacterial contamination in a fermentation process employing yeast recycle and utilizing sugars from lignocellulosic feedstocks. The chlorine dioxide was used to treat a yeast slurry separated from the fermentation prior to its reintroduction to the fermentor. WO 2007/149450 discloses a method for preventing the growth of bacterial contaminants in yeast fermentations to produce ethanol via the addition of stabilized chlorine dioxide. The stabilized chlorine dioxide was added prior to any significant propagation of bacteria in the system, such as to the inoculant or to fermentable sugars before their introduction to the fermentation system. As the pH of the solution is lowered due to the generation of organic acids produced by bacterial contaminants, activated chlorine dioxide is generated in situ from the stabilized chlorine dioxide and further growth of the bacteria was prevented. Johnson and Kunz (The New Brewer, 1998, Coming Clean—A New Method of Washing Yeast Using Chlorine Dioxide Vol. 15 #5-P56) discloses the use of chlorine dioxide to wash yeast during the brewing of beer as an alternative to acid washing.

The effects of $ClO_2$ concentration on bacterial cell kill and yeast viability and fermentative capacity have been examined in ethanol fermentations (see co-owned and co-pending WO 2009/026706), but less information is available regarding the effect of other variables on chlorine dioxide efficacy, such as pH. However, the impact of pH on the effectiveness of chlorine dioxide in other industrial applications has been studied. In the beverage industry, it has been reported that chlorine dioxide has a constant efficacy at a pH level between 4 and 10, with the rate of sterilization being greater at high pH. ("Chlorine Dioxide in the Beverage Industry", Petplanet Insider, September 2005, 6:46-47). Chlorine dioxide bleaching stages in pulp bleaching applications are conducted at acidic pH values, although there is still some controversy about the optimal pH (Reeve, 1996, Section IV: The Technology of Chemical Pulp Bleaching, Chapter 3: Chlorine Dioxide in Delignification In Pulp Bleaching, Principles and Practice, Ed. by Dence and Reeve, Tappi Press). Foegeding et al. (1986, Journal of Food Science, 51(1):197-201) assessed chlorine dioxide inactivation of *Bacillus* and *Clostridium* spores in water buffered at pH values of 4.5, 6.5 and 8.5 with phosphoric acid and it was found that *C. perfuringens* spores were inactivated more at pH 8.5 than at 6.5.

SUMMARY OF THE INVENTION

The present invention provides a method for producing a fermentation product. More specifically, the present invention relates to a method for the production of a fermentation product from a sugar hydrolysate.

Disclosed herein is an improved method for the production of a fermentation product from a sugar hydrolysate.

According to a first aspect of the invention, there is provided a method (A) for producing a fermentation product from a sugar hydrolysate comprising: (i) fermenting the sugar hydrolysate in a fermentation system to produce a fermentation broth comprising a fermentation product; (ii) introducing acid and an oxidant, including but not limited to chlorine dioxide, to said fermentation system so as to expose any microbial contaminants in said fermentation system at one or more stages to chlorine dioxide at a pH of less than 3.0; and (iii) recovering the fermentation product.

According to a second aspect of the invention, there is provided a method (B) for obtaining a fermentation product from a sugar hydrolysate comprising: (i) removing suspended fiber solids from the sugar hydrolysate to obtain a clarified sugar solution; (ii) fermenting sugar in the clarified sugar solution in a fermentation reaction using yeast to produce a fermentation broth comprising the fermentation product; (iii) separating the yeast from the fermentation broth to produce a yeast slurry and a fermentation product, (iv) introducing acid and chlorine dioxide to the yeast slurry so as to expose any microbial contaminants and yeast in said yeast slurry to chlorine dioxide at a pH of less than 3.0; (v) re-introducing at least a portion of the chlorine dioxide-treated yeast slurry back to the step of fermenting, step (ii), to maintain the concentration of yeast in the fermentation reaction; and (vi) recovering the fermentation product.

In embodiments of either of the foregoing aspects of the invention, the sugar hydrolysate comprises at least xylose or glucose. In another embodiment, the sugar hydrolysate comprises both xylose and glucose. The sugar hydrolysate may be obtained from a lignocellulosic feedstock. This may involve a step of pretreating the lignocellulosic feedstock with acid or alkali.

According to another embodiment of either aspect of the invention, the acid and oxidant are introduced to said fermentation system so as to continuously expose any microbial contaminants in said fermentation system at one or more stages to the oxidant at a pH of less than 3.0

Without being limiting, the product produced by the fermentation may be either ethanol or xylitol. If ethanol is the fermentation product, it may be produced by a *Saccharomyces* spp. that converts glucose and xylose to ethanol. If xylitol is the fermentation product, it may be produced by a *Candida* spp. that converts xylose to xylitol.

According to embodiments of either aspect of the invention, in the step of introducing, the chlorine dioxide is at a concentration of between about 0.5 and about 1500 ppm. In one example of the invention, the chlorine dioxide is at a concentration of between about 100 and about 500 ppm. Preferably, microbial contaminants and yeast are exposed to chlorine dioxide at a pH of greater than about 1.0 but less than 2.5. In a further embodiment of the invention, the pH is greater than or equal to 1.0 and less than or equal to 2.5. In an example of the invention, the acid is added prior to the chlorine dioxide.

When yeast recycle is employed according to the second aspect of the invention, the clarified sugar solution resulting from the fiber solids removal step may comprise one or more sugar selected from the group consisting of glucose, xylose, galactose, mannose, arabinose, fucose and fructose. In further embodiments of this aspect of the invention, the step of fermenting may be conducted in one of a series of fermentation reactors and the chlorine dioxide-treated yeast slurry is then re-introduced back to the same or a different fermentation reactor in the series. Preferably, when the yeast slurry is treated with acid and chlorine dioxide, the temperature of the yeast slurry is between about 4° C. and about 37° C.

The concentration of microbial contaminants in the yeast slurry may be reduced to at least 100-fold lower than that of the yeast. In another embodiment, the concentration of microbial contaminants in the yeast slurry is reduced to below about $10^3$ CFU/mL.

In yet a further embodiment, the concentration of yeast cells in the yeast slurry is from about 10 g/L to about 300 g/L, or from about 20 g/L to about 200 g/L (dry cell weight).

The present invention overcomes difficulties in the prior art in connection with the efficient conversion of feedstock to ethanol or other fermentation products due to the presence of microbial contaminants. In particular, the invention is based on the discovery that the combined effect of an oxidant and low pH can result in significant improvements in reducing microbial contaminants in fermentation systems. Advantageously, the process of the present invention may not result in any substantial reduction in the viability or fermentative capacity of the yeast. Therefore, the yield of the desired fermentation product and the purity of the product resulting from the fermentation can be significantly improved compared to conventional systems. Moreover, due to improved efficacy at lower pH, lower levels of an oxidant may be required relative to processes not operated at pH values below 3.0. Advantageously, this could reduce the chemical demand and thus the cost of the process.

BRIEF DESCRIPTION OF THE DRAWINGS

These and other features of the invention will become more apparent from the following description in which reference is made to the appended drawings wherein.

DETAILED DESCRIPTION

Figure 1:
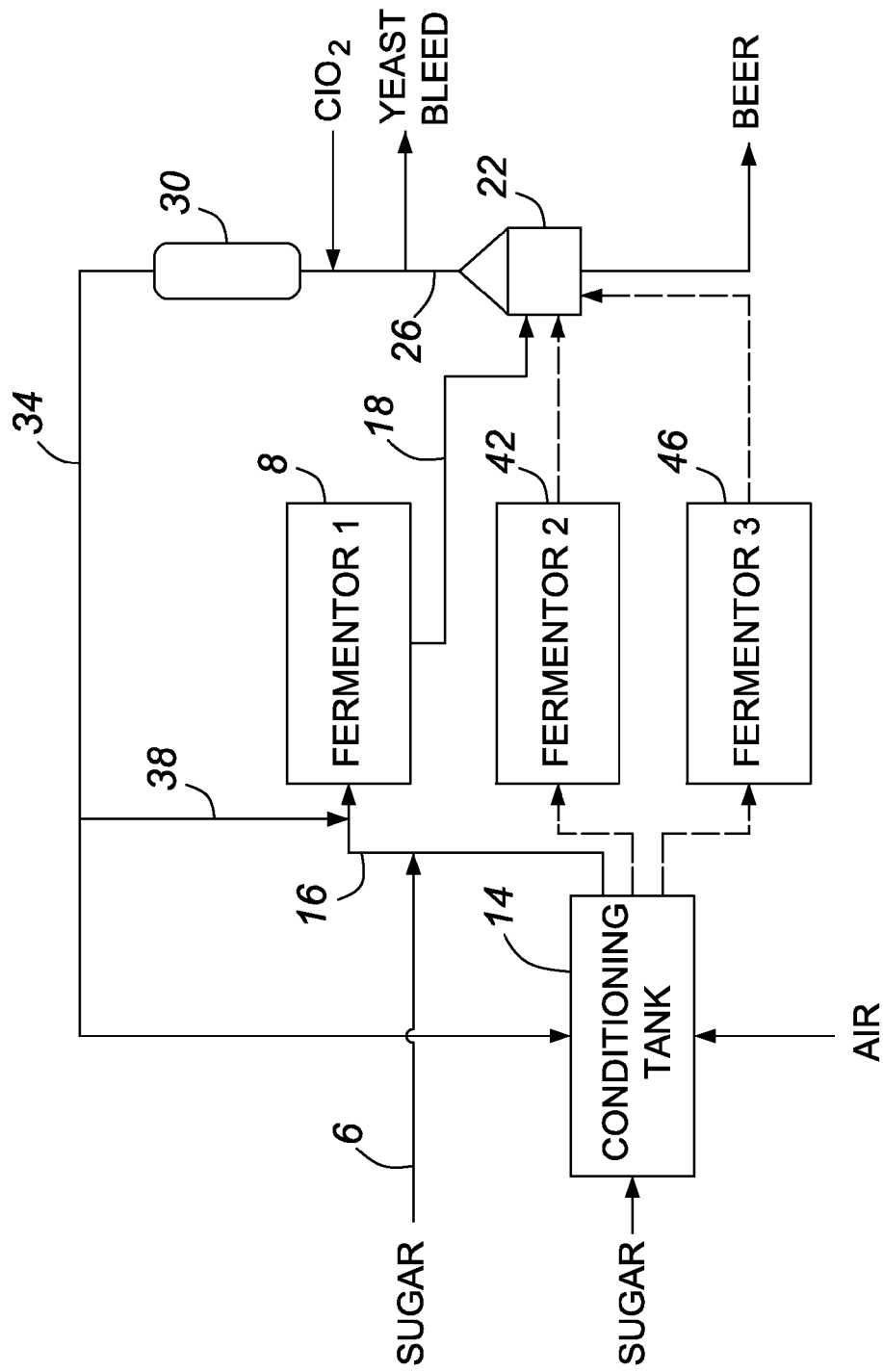
FIG. 1 shows a process flow diagram illustrating yeast recycle during fermentation with addition of acid followed by chlorine dioxide to a yeast slurry (also referred to herein as "yeast cream") obtained after separation of the yeast from the fermentor according to an embodiment of the invention.

The present invention relates to a method for the production of a fermentation product from a lignocellulosic feedstock.

The following description is of an embodiment by way of example only and without limitation to the combination of features necessary for carrying the invention into effect.

The sugar hydrolysate for the process may be derived from sugar and starch crops including, but not limited to, wheat, corn, sugar beets and sugar cane. Methods for producing sugar hydrolysates containing fermentable sugar from such feedstocks are well known.

The feedstock for the process of the present invention may also be a lignocellulosic material, which includes any type of plant biomass such as, but not limited to, non-woody plant biomass, cultivated crops such as, but not limited to grasses, for example, but not limited to, C4 grasses, such as switch grass, cord grass, rye grass, miscanthus, reed canary grass, or a combination thereof, sugar processing residues, for example, but not limited to, baggase, such as sugar cane bagasse, beet pulp, or a combination thereof, agricultural residues, for example, but not limited to, soybean stover, corn stover, rice straw, rice hulls, barley straw, sugar cane straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the lignocellulosic feedstock may comprise cellulosic waste material or forestry waste materials such as, but not limited to, newsprint, cardboard and the like. Lignocellulosic feedstock may comprise one species of fiber or, alternatively, lignocellulosic feedstock may comprise a mixture of fibers that originate from different lignocellulosic feedstocks.

Lignocellulosic feedstocks comprise cellulose in an amount greater than about 20%, more preferably greater than about 30%, more preferably greater than about 40% (w/w). For example, the lignocellulosic material may comprise from about 20% to about 50% (w/w) cellulose, or any amount therebetween. The lignocellulosic feedstock also comprises lignin in an amount greater than about 10%, more typically in an amount greater than about 15% (w/w). The lignocellulosic feedstock may also comprise small amounts of sucrose, fructose and starch. Additionally, the feedstock may contain pectin.

The present invention may be practiced with a lignocellulosic feedstock material that has been pretreated. Pretreatment methods are intended to deliver a sufficient combination of mechanical and chemical action so as to disrupt the fiber structure and increase the surface area of feedstock to make it accessible to hydrolytic enzymes such as cellulases. Mechanical action typically includes the use of pressure, grinding, milling, agitation, shredding, compression/expansion and chemical action includes the use of acid or alkali, often in combination with heat, and solvents.

The pretreatment is preferably a chemical treatment involving the addition of acid or alkali. This includes any acid or alkali that is suitable for disrupting fiber structure of the lignocellulosic feedstock and increasing accessibility of the lignocellulosic feedstock to being hydrolysed in a subsequent enzymatic hydrolysis. Non-limiting examples of suitable acid and alkali for such purpose include sulfuric acid, nitric acid, hydrochloric acid, sulfurous acid, phosphoric acid, ammonia, ammonium hydroxide, sodium hydroxide, potassium hydroxide, lime and magnesium hydroxide.

Pretreatment with acid hydrolyses the hemicellulose, or a portion thereof, that is present in the lignocellulosic feedstock to the monomeric sugars including, but not limited to, xylose, arabinose, mannose, and/or galactose, and organic acids, such as acetic acid, galacturonic acid and glucuronic acid. Sucrose, fructose and starch may also be present in the sugar hydrolysate. Preferably, the acid pretreatment is performed so that nearly complete hydrolysis of the hemicellulose and a small amount of conversion of cellulose to glucose occurs. The cellulose is hydrolysed to glucose in a subsequent step that uses cellulase enzymes and beta-glucosidase. Typically a dilute acid, at a concentration from about 0.02% (w/v) to about 2% (w/v), or any amount therebetween, (measured as the percentage weight of pure acid in the total weight of dry feedstock plus aqueous solution) is used for the pretreatment. Preferably, the acid pretreatment is carried out at a temperature of about 180° C. to about 250° C., or any temperature therebetween, for a time of about 60 seconds to about 600 seconds, or any time therebetween, at a pH of about 0.8 to about 2.0, or any pH therebetween.

One method of performing acid pretreatment of the feedstock is steam explosion, using the process conditions described in U.S. Pat. No. 4,461,648 (which is incorporated herein by reference). Another method of pretreating the feedstock slurry involves continuous pretreatment, meaning that the lignocellulosic feedstock is pumped through a reactor continuously. Continuous acid pretreatment is familiar to those skilled in the art, see, for example, U.S. Pat. No. 5,536,325, WO 2006/128304 and U.S. Pat. No. 4,237,226 (which are incorporated herein by reference). Other techniques that are known in the art and that may be used as required, include, but are not limited to, those disclosed in U.S. Pat. No. 4,556,430 (which is incorporated herein by reference).

After pretreatment, the lignocellulosic feedstock may be separated to obtain a solids stream comprising the pretreated feedstock and an aqueous stream comprising soluble components. This may be carried out by washing the pretreated feedstock with an aqueous solution to produce a wash stream, and a solids stream comprising the pretreated feedstock. Alternatively, the pretreated feedstock is subjected to a solids-liquid separation, using known methods such as centrifugation, microfiltration, plate and frame filtration, crossflow filtration, pressure filtration, vacuum filtration and the like. When an acidic pretreatment is employed, the aqueous phase comprises sugars produced by the hydrolysis of hemicellulose, as well as the acid added during the pretreatment and any organic acids liberated during the pretreatment. This stream may be subsequently processed to remove the mineral and organic acids, and then optionally fed back to the solids stream comprising the pretreated feedstock. The aqueous stream obtained from the acid pretreated feedstock may also be fermented. For example, xylose present in this stream may be fermented to alcohols, including ethanol and butanol; sugar acids including xylonic acid and arabonic acid; sugar alcohols including xylitol, arabitol, erythritol, galactitol and mannitol; organic acids including citric acid, malic acid, succinic acid, pyruvic acid, acetic acid, itaconic acid and lactic acid; ketones including acetone; and amino acids, including glutamic acid.

The pretreated lignocellulosic feedstock is typically slurried in an aqueous solution such as process water, fresh water, steam condensate or process recycle streams. The concentration of pretreated lignocellulosic feedstock in the slurry depends on the particle size, water retention, pump capacity and other properties of the feedstock. Typically, the concentration is between about 3% and 30% (w/w), or any amount therebetween of fiber solids (also known as suspended or undissolved solids), or between about 10% and about 20% (w/w) fiber solids, or any amount therebetween. The fiber solids concentration can be higher if dewatering of the feedstock slurry is carried out prior to pretreatment, for example as set forth in PCT/CA2009/001191 (incorporated herein by reference). The aqueous slurry preferably has a solids concentration that enables it to be pumped. It is preferred that the fiber solids comprise at least about 20% to about 70% cellulose by weight, or any weight percent therebetween. For example, the fiber solids may comprise 20%, 25%, 30%, 35%, 40%, 45%, 50%, 55%, 60%, 65% or 70% by weight cellulose.

The pH of the pretreated feedstock is typically adjusted so that it is within a range which is optimal for the cellulase enzymes used. Generally, the pH of the pretreated feedstock is adjusted to within a range of about 3.0 to about 7.0, or any pH therebetween. For example, the pH may be within a range of about 4.0 to about 6.0, or any pH therebetween, between about 4.5 and about 5.5, or any pH therebetween, or about 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0 or any pH therebetween.

The temperature of the pretreated feedstock is adjusted so that it is within the optimum range for the activity of the cellulase enzymes. Generally, a temperature of about 45° C.

to about 55° C., or any temperature therebetween, is suitable for most cellulase enzymes, for example a temperature of 45, 46, 48, 49, 50, 51, 52, 53, 54, 55° C., or any temperature therebetween.

The cellulase enzymes and the β-glucosidase enzyme are added to the pretreated feedstock, prior to, during, or after the adjustment of the temperature and pH of the aqueous slurry after pretreatment. Preferably the cellulase enzymes and the β-glucosidase enzyme are added to the pretreated lignocellulosic feedstock after the adjustment of the temperature and pH of the slurry.

By the term "cellulase enzymes" or "cellulases," it is meant a mixture of enzymes that hydrolyse cellulose. The mixture may include cellobiohydrolases (CBH), endoglucanases (EG) and β-glucosidase. In a non-limiting example, a cellulase mixture may include CBH, EG and β-glucosidase enzymes. The CBH enzyme primarily hydrolyses cellulose polymer chains from their ends to release cellobiose and the EG enzyme primarily hydrolyses cellulose polymer in the middle of the chain. If the pretreated feedstock comprises xylan, it is especially advantageous if the enzyme hydrolysis is also carried out in the presence of one or more xylanase enzymes. Examples of xylanase enzymes that may be used for this purpose include xylanase 1, 2 and β-xylosidase, which are typically present in cellulase mixtures.

The conversion of cellobiose to glucose is carried out by the enzyme β-glucosidase. By the term "β-glucosidase", it is meant any enzyme that hydrolyses the glucose dimer, cellobiose, to glucose. The activity of the β-glucosidase enzyme is defined by its activity by the Enzyme Commission as EC 3.2.1.21.

The process of the present invention can be carried out with any type of cellulase enzymes suitable for hydrolysing cellulose to glucose, regardless of their source. Non-limiting examples of cellulases which may be used in the practice of the invention include those obtained from fungi of the genera *Aspergillus*, *Humicola*, *Chrysosporium*, *Myceliophtora*, *Penicillium*, *Neurospora*, *Hypocrea* and *Trichoderma*, and from bacteria of the genera *Bacillus* and *Thermobifida*.

The cellulase enzyme dosage is chosen to convert the cellulose of the pretreated feedstock to glucose. For example, an appropriate cellulase dosage can be about 0.1 to about 40.0 Filter Paper Units (FPU or IU) per gram of cellulose, or any amount therebetween, for example 0.1, 0.5, 1.0, 2.0, 4.0, 6.0, 8.0, 10.0, 12.0, 14.0, 16.0, 18.0, 20.0, 22.0, 24.0, 26.0, 28.0, 30.0, 32.0, 34.0, 36.0, 38.0, 40.0 FPU (or IU) per gram of cellulose, or any amount therebetween.

The enzymatic hydrolysis with cellulase enzymes produces a solution comprising glucose, unconverted cellulose and lignin. Other components that may be present in the hydrolysate slurry include xylose, arabinose, mannose and galactose, acetic acid, glucuronic acid and galacturonic acid, as well as silica, insoluble salts and other compounds.

Although the production of a sugar hydrolysate by pretreatment, followed by cellulose hydrolysis of the pretreated feedstock with cellulase enzymes has been described, it should be understood that the aqueous sugar stream may arise from an acid or alkali treatment to effect a complete hydrolysis of the hemicellulose and cellulose components of the feedstock to their respective monomeric constituents. The hydrolysis may be carried out in two stages (see U.S. Pat. No. 5,536,325, which is incorporated herein by reference), or may be performed in a single stage.

In accordance with the invention, a sugar hydrolysate is fermented by one or more than one yeast to produce a fermentation broth comprising the fermentation product. The sugar hydrolysate may arise from various stages in the processing of the feedstock. As described previously, a hemicellulose hydrolysate separated from a solids stream comprising the pretreated feedstock may be sent to fermentation. This sugar hydrolysate will typically comprise xylose, glucose, arabinose, mannose and galactose. After separation of the hemicellulose hydrolysate from the solids, the cellulose in the pretreated feedstock may be subjected to enzymatic hydrolysis to yield glucose and the resultant glucose stream may then be sent to fermentation. Alternatively, a stream of pretreated feedstock comprising cellulose as well as monomeric sugars resulting from hemicellulose hydrolysis is subjected to enzymatic hydrolysis with cellulase enzymes. This yields a sugar hydrolysate comprising sugars liberated from hemicellulose during pretreatment, as well as glucose resulting from the enzymatic hydrolysis of cellulose. In a further embodiment, a hemicellulose hydrolysate is separated from the pretreated feedstock and then is added to the stream comprising glucose obtained from the enzymatic hydrolysis of cellulose, thereby producing a stream comprising both glucose and monomeric sugars derived from hemicellulose, which in turn is sent to fermentation. In yet a further embodiment of the invention, the sugar hydrolysate sent to fermentation is obtained by a complete acid or alkali hydrolysis in which both the cellulose and hemicellulose components of the feedstock are hydrolysed to their monomeric constituents.

In a preferred embodiment, the sugar hydrolysate sent to fermentation is substantially free of undissolved solids, such as lignin and other unhydrolysed components. This is particularly advantageous in embodiments of the invention employing a subsequent step of separating and recycling the yeast from the fermentation broth since it is desirable to avoid any significant recycle of undissolved solids along with the yeast. The separation may be carried out by known techniques, including centrifugation, microfiltration, plate and frame filtration, crossflow filtration, pressure filtration, vacuum filtration and the like.

Any one of a number of known yeasts may be used to convert sugar in the sugar hydrolysate to ethanol or other fermentation products. This includes, but is not limited to yeast from the genera *Saccharomyces*, *Hansenula*, *Pichia*, *Kluyveromyces* and *Candida*. Additionally, commercially available yeasts may be used, including, but not limited to Turbo yeast, Ethanol Red® Safdistil®, Thermosac®, Fermiol®, Fermivin® or Superstart™. The yeast may be genetically engineered to ferment both hexose and pentose sugars to ethanol. Alternatively, the yeast may be a strain that has been made capable of xylose and glucose fermentation by one or more non-recombinant methods, such as adaptive evolution or random mutagenesis and selection.

For example, the fermentation may be performed with recombinant *Saccharomyces* yeast. The recombinant yeast may be a strain that has been made capable of xylose fermentation by recombinant incorporation of (a) genes encoding xylose reductase (XR) and xylitol dehydrogenase (XDH) (see for example, U.S. Pat. Nos. 5,789,210, 5,866,382, 6,582,944 and 7,527,927 and EP 450 530) and/or (b) gene(s) encoding one or more xylose isomerase (XI) (see for example, U.S. Pat. Nos. 6,475,768 and 7,622,284). In addition, the modified yeast strain may also overexpress an endogenous or heterologous gene encoding xylulokinase (XK).

Other yeast besides *Saccharomyces cerevisiae* can ferment hexose and pentose sugars to ethanol. This includes, but is not limited to, yeast of the genera *Hansenula*, *Pichia*, *Kluyveromyces* and *Candida*. WO 2008/130603 discloses *Hansenula polymorpha* strains with increased production of ethanol from xylose. Moreover, *Pichia stipitis* and *Candida shehatae* mutants have been isolated by the method disclosed in U.S. Pat. No. 5,126,266.

In another example of the invention, the xylose is converted to a sugar alcohol. The sugar alcohol may be selected from xylitol, arbitol, erythritol, mannitol and galactitol. Preferably, the sugar alcohol is xylitol. In one embodiment of the invention, the xylose is fermented to xylitol by yeast. Yeasts that are capable of converting xylose to xylitol include strains of *Candida, Pichia, Pachysolen, Hansenula, Debaryomyces, Kluyveromyces, Saccharomyces* and *Schizosaccharomyces*. According to one embodiment of the invention, the yeast strain is *Candida*, preferably *C. tropicalis*.

The fermentation may be performed at or near the temperature and pH optima of the fermentation microorganism. The temperature range for the fermentation may be between about 10° C. to about 70° C., although the temperature may be higher if the yeast is naturally or genetically modified to be thermostable. In one embodiment of the invention, the temperature is from about 10° C. to about 55° C., or any temperature therebetween, or about 15° C. to about 45° C., or any temperature therebetween. The pH of the fermentation may be between about 3 and about 6, or any pH therebetween, for example, a pH of 3.0, 3.5, 4.0, 4.5, 5.0, 5.5, 6.0, or any pH therebetween. The inoculum of the fermentation microorganism will depend on other factors, such as the activity of the fermentation microorganism, the desired fermentation time, the volume of the reactor and other parameters. It will be appreciated that these parameters may be adjusted as desired by one of skill in the art to achieve optimal fermentation conditions.

The sugar hydrolysate may also be supplemented with additional nutrients required for growth and fermentation performance of the fermentation microorganism. For example, yeast extract, specific amino acids, phosphate, nitrogen sources, salts, trace elements and vitamins may be added to the sugar hydrolysate to support growth and optimize productivity of the microorganism. (See also Verduyn et al., 1992, Yeast 8(7):501-170, Jørgensen, 2009, Appl Biochem Biotechnol, 153:44-57 and Zhao et al., 2009, Journal of Biotechnology, 139:55-60, which are each incorporated herein by reference). Typically the fermentation is conducted under anaerobic conditions, although aerobic or microaerobic fermentations are also included within the scope of the invention.

The term "fermentation system", includes any arrangement of one or more fermentation reactors for fermenting sugars to a fermentation product by yeast. In an embodiment of the invention, this includes systems that employ yeast recycle. The fermentation system may also comprise tanks for conditioning the yeast. In a typical, commercial-scale operation, the fermentation is conducted in a system using multiple reactors, such as 2 to 6, or any number therebetween. The fermentation reactors may be arranged in series or parallel. The fermentation may be conducted in batch, continuous or fed-batch modes, with or without agitation. In one embodiment of the invention, the fermentation reactor(s) is agitated lightly.

The microbial contaminants are exposed to the oxidant at a pH that is less than 3.0 by the addition of acid. The pH may be greater than about 1, but less than 3.0. This includes all subvalues therebetween, for example a pH of 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8 or 2.9, or any pH therebetween, is included within the scope of the invention. Examples of pH ranges that may be employed include about 1.0 to 3.0, 1.0 to 2.9, 1.0 to 2.8, 1.0 to 2.75, 1.0 to 2.5, 1.0 to 2.4, 1.0 to 2.3, 1.0 to 2.2, 1.0 to 2.1 or 1.0 to 2.0.

In one embodiment of the invention, the acid is a mineral acid such as sulfuric acid, hydrochloric acid, sulfurous acid, phosphoric acid or nitric acid.

Any stream from the fermentation system containing microbial contaminants may be exposed to the oxidant at a pH of less than 3.0. Typically such streams will also comprise yeast, along with the microbial contaminants, although the oxidant and the acid could be introduced to decontaminate a sugar hydrolysate prior to the addition of yeast.

The acid may be added prior to oxidant addition or a mixture of the oxidant and acid may be introduced to the fermentation system. The oxidant reacts quickly and thus it is typically not advantageous to add it prior to acid addition.

In embodiments of the invention employing yeast recycle, the acid may be added first to the yeast slurry that is separated from the fermentation broth, followed by addition of the oxidant. Alternatively, a mixture of the acid and oxidant is added to the yeast slurry prior to the oxidant treatment.

An oxidant suitable for use in the invention reduces bacterial contaminants to a level whereby they no longer reduce productivity or product yield of the fermentation. The oxidant should not have any significant effect on yeast viability or fermentative capacity. Moreover, the oxidant selected for use in the invention possesses maximum effectiveness at reducing bacterial contaminants at a pH of less than 3.0, or less than 2.5. A suitable oxidant can be selected by those of ordinary skill in the art by routine experimentation. Without being limiting, the oxidant may be chlorine dioxide or ozone.

Preferably, the oxidant treatment reduces the concentration of microbial contaminants (in colony forming units per mL of culture or CFU/mL) to about 100-fold less than the concentration of yeast. More preferably, the oxidant treatment reduces the concentration of microbial contaminants to about $10^3$ CFU/mL or less. For example, the oxidant treatment may reduce the concentration of microbial contaminants from about $10^{10}$ to about $10^3$ CFU/mL. Bacterial colonies are enumerated via standard plate count methods. Methods are known for selectively plating bacterial colonies and inhibiting yeast growth. An example of such a method involves preparing serial dilutions and plating on agar plates containing cyclohexamide, which selectively kills yeast but not bacteria (see for example, Example 1.1).

The oxidant may be introduced to the fermentation system comprising yeast and microbial contaminants at a concentration of about 0.5 ppm and about 1500 ppm, or any concentration therebetween. In a continuous system, the oxidant would typically be added to one or more streams containing microbial contaminants. In another embodiment of the invention, the oxidant, including, but not limited to chlorine dioxide may be added at a concentration between about 60 and about 1000 ppm or between about 75 and about 1000 ppm, including between about 75 ppm and about 500 ppm, or between about 80 and about 1000 ppm or between about 90 and about 1000 ppm or between about 100 and about 500 ppm, or any concentration therebetween. For example, the oxidant, including but not limited to chlorine dioxide, may be added at a concentration of 0.5, 5, 10, 20, 30, 40, 50, 55, 60, 70, 75, 80, 85, 90, 95, 100, 200, 300, 400, 500, 600, 700, 800, 900, 1000, 1100, 1200, 1300, 1400 or 1500 ppm, or any concentration therebetween. However, depending on the oxidant used, a higher dose than this may be required.

The chlorine dioxide may be generated using known methods, for example, by reacting chlorine gas with water and then adding sodium chlorite, or by reacting sodium hypochlorite with an acid and adding sodium chlorite. In one example of the invention, stabilized chlorine dioxide (SCD) is acidified and the chlorine dioxide then produced can be introduced to the fermentation such as to the acidified yeast slurry if yeast recycle is utilized. Alternatively, after acid addition, SCD can be added directly to the fermentation. In this latter example, chlorine dioxide will be generated in situ. (See for example, Kim et al., 2008, Food Microbiology, 25:964-969 and WO 2007/149450).

The oxidant treatment is preferably conducted at a temperature of between about 4° C. and about 40° C., or any temperature therebetween, for example 4, 6, 8, 10, 12, 14, 16, 18, 20, 22, 24, 26, 28, 30, 32, 34, 36, 38, 40° C., or any temperature therebetween. The duration of the treatment may be from 5 seconds to about 60 min, or any time therebetween, for example 5, 15, 20, 25, 30, 35, 40, 45 or 50 seconds, or 10, 20, 30, 40, 50, 60 minutes or any time therebetween. As would be appreciated by those of ordinary skill in the art, reactions involving chlorine dioxide can proceed quickly or even instantaneously. Accordingly, when this oxidant is utilized, shorter residence times may be utilized or the residence time may be eliminated altogether. However, the practice of this invention is not limited by any particular choice of residence time during the oxidant treatment as instantaneous reaction rates are also contemplated.

In those embodiments employing yeast recycle, the concentration of cells in the yeast slurry (also referred to herein as "yeast cream") that is exposed to the oxidant and acid is typically from about 50 g/L to about 300 g/L (dry cell weight). For example, the concentration of cells in the yeast slurry may be 50, 60, 70, 80, 90, 100, 110, 120, 130, 140, 150, 160, 180, 200, 220, 240, 260, 280 or 300 g/L (dry cell weight). More preferably, the concentration of cells in the yeast slurry is from about 50 g/L to about 300 g/L, or from about 150 g/L to about 250 g/L, or from about 175 g/L to about 225 g/L (dry cell weight).

The fermentation may be conducted so that the yeast are separated from the fermentation and sent back to the fermentation reaction (also referred to herein as "yeast recycle"). This involves withdrawing fermentation broth from the fermentation reactor and separating the yeast from this solution by known separation techniques to produce a yeast slurry. Examples of suitable separation techniques include, but are not limited to, centrifugation, microfiltration, plate and frame filtration, crossflow filtration, pressure filtration, settling, vacuum filtration and the like. In one example of the invention, the recycle is continuous, meaning the yeast is continuously recycled through the fermentation system. In an alternative embodiment, the yeast recycle is operated in batch mode.

After treatment of the acidified yeast slurry with the oxidant, the oxidant-treated yeast slurry is re-introduced back to the fermentation reaction. A yeast purge may be employed after separation of the yeast from the fermentation and prior to exposure to the oxidant and low pH. Preferably, between about 10% and about 99%, or any amount therebetween, of the total yeast cells in the yeast slurry are treated with the oxidant and acid and then recycled. More preferably, between 80% and 95% of the yeast cells are treated and recycled and most preferably, at least 90% of the yeast cells are treated and recycled.

It should be understood that the practice of the invention is not limited by the number of cycles of yeast cell recycle. Yeast recycle may be repeated at least once, or between 5 and 70 times, or even more times than this. Without intending to be limiting in any manner, yeast recycle may be repeated 5, 10, 15, 20, 25, 30, 35, 40, 45, 50, 55, 60, 65 or 70 times. It should also be understood, that the oxidant treatment need not be performed with every recycle. Treatment frequency may be adjusted by one of ordinary skill in the art as desired to optimize performance and minimize bacterial numbers.

The fermentation may employ multiple fermentation reactors. In such embodiments, yeast is withdrawn from a reactor in the system, treated with the acid and chlorine dioxide or other suitable oxidant and then re-introduced back to one or more of the fermentation reactors or a conditioning or recovery reactor. The acidified, oxidant-treated yeast may be fed back to the same reactor in the series or a different reactor. By re-circulating the yeast in this manner, their concentration is maintained and conditioned to lignocellulosic hydrolysate which increases the volumetric rate of the reaction and also maximizes the yield to the desired product by minimizing the diversion of carbon and other nutrients to bacteria cell production.

Referring now to FIG. 1 there is depicted a fermentation system with recycle of yeast. FIG. 1 is included as an example of how the present invention can be practised and is not meant to be limiting in any manner. That is, the invention may be practised with or without yeast recycle.

An aqueous sugar hydrolysate 6 obtained from pretreating the lignocellulosic feedstock is fed to a first fermentation reactor 8. The sugar stream is previously treated to remove insoluble lignin and other suspended solids. The sugar stream 6 is combined with yeast from a conditioning tank 14 from line 16 or from line 38 containing recycled yeast. The conditioning tank 14, in turn, is fed with a stream containing air and a portion of sugar from stream 6. A fermented solution comprising ethanol is withdrawn from the reactor 8 via line 18 and fed to a separation unit 22, typically a centrifuge, which separates the yeast from the fermented solution. Separated beer, which contains ethanol, is sent to distillation to obtain a solution enriched in ethanol. A portion of the yeast slurry in line 26 is bled and after bleeding, the balance of the yeast is acidified then washed with an aqueous solution of chlorine dioxide at a pH of less than 3 and subsequently fed via line 26 to a holding tank 30 where they are held under appropriate conditions. The acidified, chlorine-dioxide treated yeast are then fed along line 34, which branches into line 38, which, in turn, introduces a portion of the yeast back to fermentor 8 to convert xylose to ethanol. The balance of the yeast can be sent via line 34 to the conditioning tank 14 for cell growth and subsequent to this, the yeast are sent to second fermentor 42, and the cycle is repeated once again. This cycle may then be repeated with fermentor three 46.

Although three fermentors are depicted in FIG. 1, it will be appreciated by those of ordinary skill in the art that the number of fermentors can be varied as required. Moreover, although the fermentors are shown in parallel, they may instead be arranged in series. Furthermore, it is contemplated that the holding tank 30 can be excluded, in which case the yeast are subsequently held, for example, in the fermentor 8. In yet a further variation, all of the yeast from line 34 are sent back to fermentor 8 via line 38 without a portion being diverted for conditioning. Alternatively, all the yeast in line 34 are sent to the conditioning tank 14 and subsequently sent to fermentor 2.

When ethanol is the product of the fermentation, it is recovered by distillation. The separated fermentation broth or beer sent to the distillation is a dilute alcohol solution which is substantially free of solids, including unconverted cellulose, although it may contain components added during the fermentation to support growth of the microorganisms, as well as small amounts of yeast that may remain after separation 16. The beer is preferably degassed to remove carbon dioxide and then pumped through one or more distillation columns to separate the alcohol from the other components in the beer. The column(s) in the distillation unit is preferably operated in a continuous mode, although it should be understood that batch processes are also encompassed by the present invention. Furthermore, the column(s) may be operated at any suitable pressure and heat for the distillation process may be added at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section. The remaining water may be removed from the vapour by a molecular sieve resin, by adsorption, or other methods known to those of skill in the art. The vapour may then be condensed and denatured.

The present invention will be further illustrated in the following examples. However, it is to be understood that these examples are for illustrative purposes only, and should not be used to limit the scope of the present invention in any manner.

EXAMPLES

Example 1

Chlorine Dioxide Treatments of Acidified Yeast Cream: Anti-Bacterial Efficacy and Dose Requirements Example 1.1

Synergistic Anti-Bacterial Effect of Chlorine Dioxide and pH

Dilute acid pretreated wheat straw was produced on an industrial scale as set forth in U.S. Pat. No. 4,461,648 (incorporated herein by reference) and then hydrolyzed with cellulase enzymes and β-glucosidase to produce a hydrolysate containing sugar derived from the hemicellulose and cellulose components of the feedstock. This hydrolysate was fermented in an industrial fermentation to produce ethanol with a *Saccharomyces cerevisiae* yeast strain set forth in co-pending and commonly owned, WO 2009/026706 (incorporated herein by reference). Yeast recycle was employed during the fermentation.

A yeast cream (also referred to herein as a "yeast slurry") separated from the fermentation broth and contaminated with bacteria that proliferated in the industrial fermentation was treated at 20° C. with acid alone, chlorine dioxide alone or a combination of the two. In the acid treated condition, the pH was lowered from 5.0 to 2.0 with sulfuric acid. In the chlorine dioxide treated condition, a concentrated stock of chlorine dioxide in water (10,000 ppm) was prepared by passing a mixture of chlorine and nitrogen gas through sodium chlorite columns. The resulting $ClO_2$ gas was sparged into 4 L of cold de-ionized water until the desired concentration was reached. This chlorine dioxide solution was used to treat the yeast cream.

In the combination treatment, the yeast cream was first lowered to pH 2.0 with sulfuric acid for 5 minutes and subsequently treated with the indicated bolus dose of chlorine dioxide for 5 minutes. In cases where the pH was lowered, the yeast cream was titrated back to 5.0 with sodium hydroxide after 10 minutes and prior to plating for bacterial enumeration. The duration of acid exposure was limited to 10 minutes to match the duration of exposure for the other treatments.

Bacterial colonies were enumerated via standard plate count methods. In order to selectively plate bacterial colonies and inhibit yeast growth, tryptic soy agar plates (15 g/L pancreatic digest of casein, 5 g/L enzymatic digest of soybean meal, 5 g/L sodium chloride and 15 g/L agar) with 100 mg/L cycloheximide were used. Samples were serially diluted into sterile saline (0.9% NaCl w/v) prior to plating.

Figure 2:
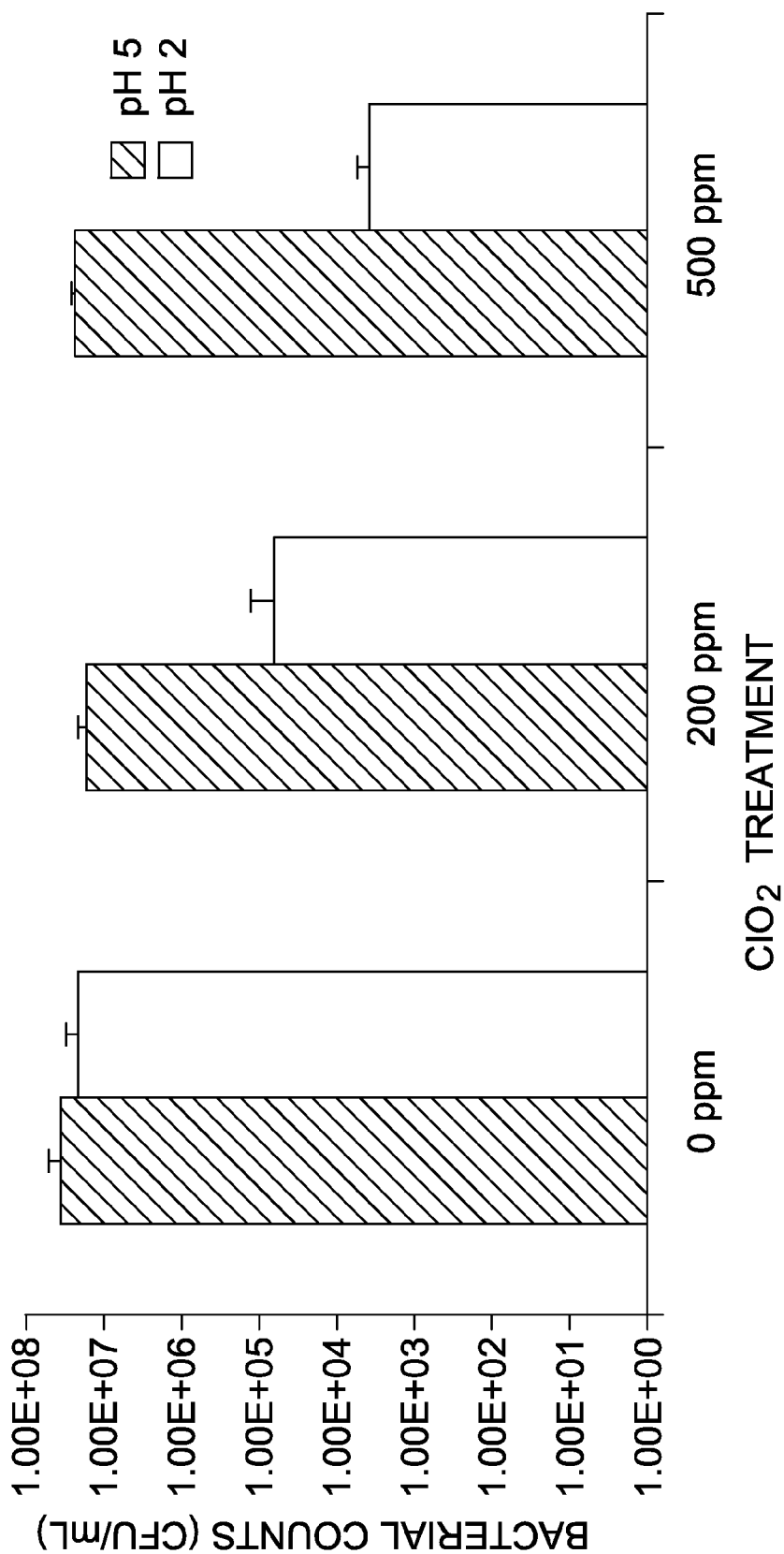
FIG. 2 is a bar graph showing bacterial counts (CFU/mL) of a contaminated yeast cream after treatment with a bolus dose of 0, 200 and 500 ppm chlorine dioxide either at pH 5 (filled bars) or preceded by titration with sulfuric acid to pH 2 (open bars).

FIG. 2 illustrates the synergistic effect of chlorine dioxide and low pH. Errors bars represent the standard deviation of the mean of duplicate experiments, each plated in triplicate. These data demonstrate that lowering the pH alone or chlorine dioxide alone are not as effective at reducing bacterial population compared to when the pH is lowered first and then followed with a chlorine dioxide treatment at the low pH. Increasing chlorine dioxide dose has a negligible effect on bacterial populations at pH 5.0 (compare filled bars at 0, 200 and 500 ppm chlorine dioxide). Similarly, lowering the pH without chlorine dioxide does not significantly reduce the bacterial population (compare closed and open bars at 0 ppm chlorine dioxide). When combined with lowered pH, chlorine dioxide treatments of 200 ppm and 500 ppm reduced the bacterial population by $10^2$ CFU/mL and $10^3$ CFU/mL, respectively (see open bars at 200 ppm and at 500 ppm).

Example 1.2

Effect of Chlorine Dioxide Dose on Bacterial Contamination of a Yeast Fermentation Culture Contaminated yeast cream obtained from the fermentation of Example 1.1 was titrated to pH 2.0 with sulfuric acid, treated with various concentrations of chlorine dioxide (0, 50, 100, 150 and 200 ppm) and plated to determine the bacterial reduction at pH 2.0 as outlined above, with the exception that the temperature of the treatment was 30° C. rather than 20° C. Bacterial populations were enumerated as previously described (Example 1.1). Bacterial populations were also enumerated on a control sample that was not subjected to chlorine dioxide or pH titration.

Figure 3:
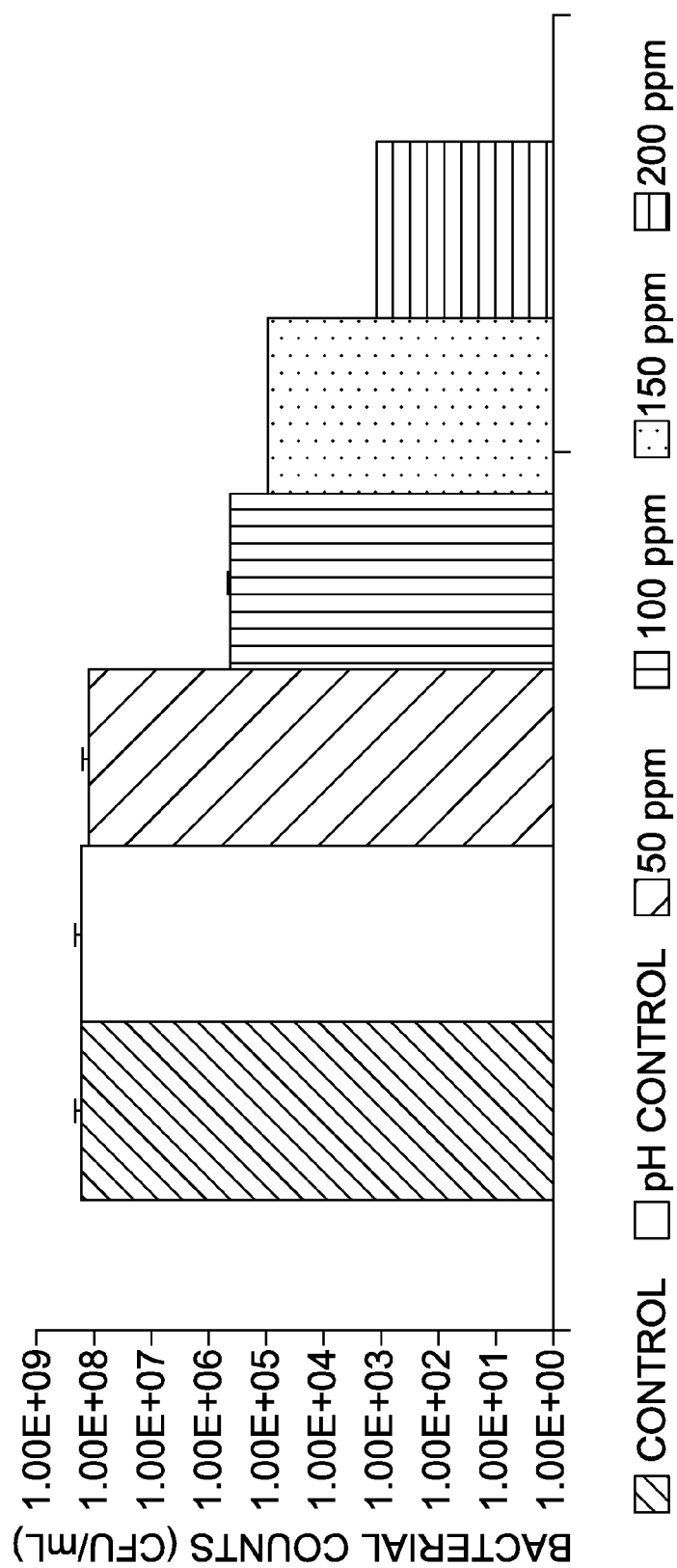
FIG. 3 is a bar graph showing bacterial counts (CFU/mL) of a contaminated yeast cream after treatment with no acid or chlorine dioxide (control), titration to pH 2 with mineral acid with no chlorine dioxide treatment (pH control) and titration to pH 2, followed by treatment with a bolus dose of 50, 100, 150 and 200 ppm chlorine dioxide.

FIG. 3 illustrates the results. Errors bars represent the standard deviation of the mean of duplicate experiments, each plated in triplicate. As shown in the figure, a chlorine dioxide dose of 100 ppm at pH 2 and 30° C. reduced contamination in a yeast cream by $10^2$ CFU/mL. Yeast cream treated with 200 ppm chlorine dioxide at 30° C. decreased bacterial counts by a magnitude of greater than $10^5$ CFU/mL, which is a greater reduction than the 500 ppm treatment at room temperature (100-fold reduction; see FIG. 2). These results demonstrate that increasing the temperature of the treatment by 10° C. further increased the reactivity of $ClO_2$, which allows for increased efficacy at decreased dosage. Notably, at 200 ppm, the $10^3$ CFU/mL dilution plates had no bacterial growth, indicating that the maximum bacterial reduction was greater than $10^5$ CFU/mL at 200 ppm. The addition of acid alone (pH control) did not reduce the bacterial population.

Example 2

Low pH and Chlorine Dioxide Anti-Bacterial Treatments on Yeast Culture Viability and Fermentation Performance A sample of the yeast cream from Example 1.1 was plated for yeast growth after the treatments outlined therein. That is, contaminated yeast creams were treated at 20° C. with sulfuric acid alone at pH 2 or in combination with chlorine dioxide at 0, 200 and 500 ppm. Selective yeast growth was enabled by serially diluting the cream in sterile saline (0.9% NaCl w/v) and plating on YM plates (10 g/L glucose, 5 g/L peptone, 3 g/L yeast extract, 3 g/L malt extract, 20 g/L agar) containing 34 mg/L chloramphenicol to inhibit bacterial growth.

Figure 4:
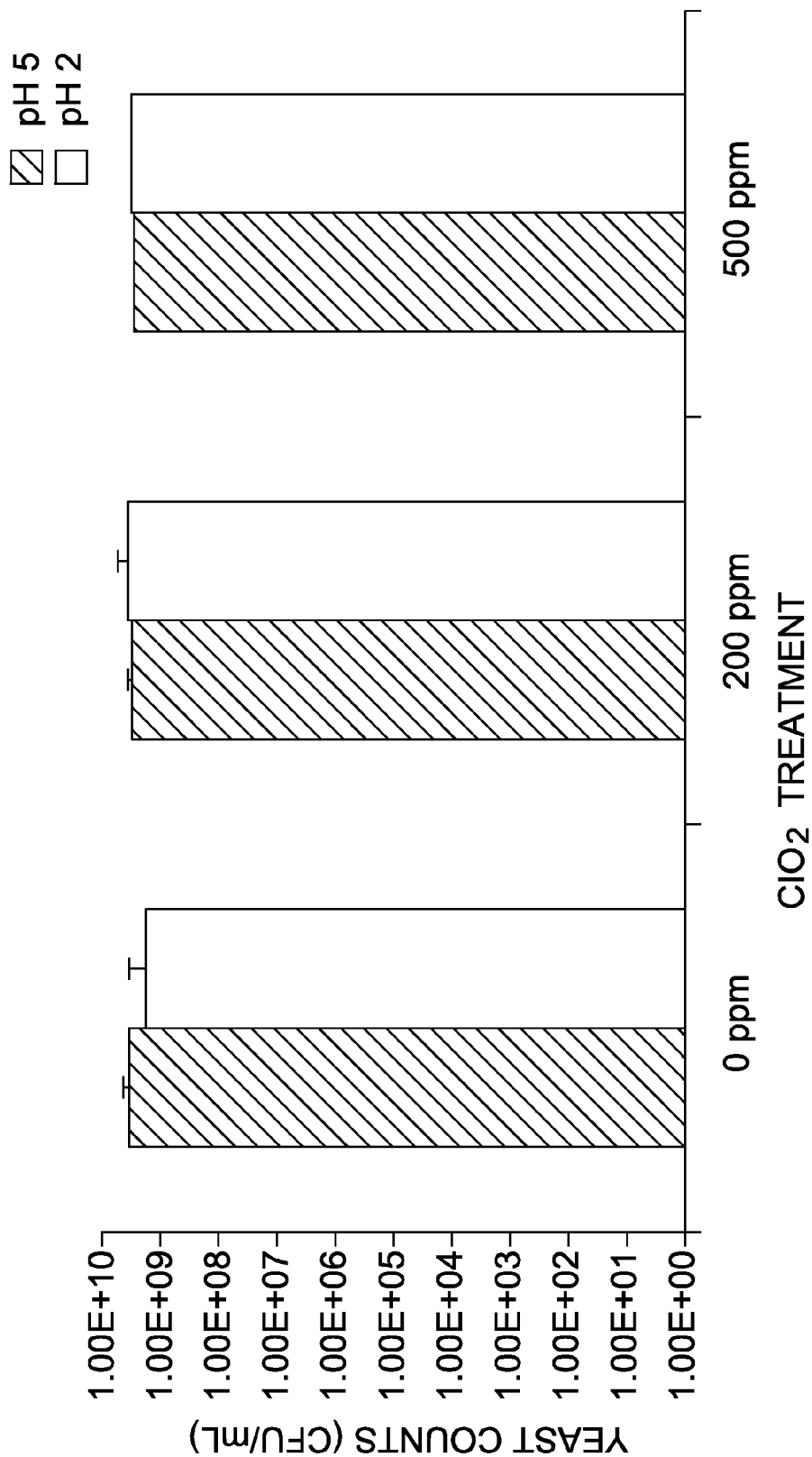
FIG. 4 is a bar graph showing yeast cell counts (CFU/mL) of a contaminated yeast cream after treatment with 0, 200 and 500 ppm chlorine dioxide either at pH 5 (filled bars) or preceded by titration with sulfuric acid to pH 2 (open bars).

The results are shown in FIG. 4. Error bars represent the standard deviation of the mean of duplicate experiments, each plated in triplicate. The figure clearly indicates that the viability of the fermentation yeast culture is not affected by either the acid treatment or the combination of acid and chlorine dioxide. As can be seen, increasing chlorine dioxide dose has a negligible effect on fermentation yeast populations regardless of the pH of the treatment.

Yeast fermentation performance was evaluated by inoculating the contaminated control yeast, acid-treated yeast and combination acid-chlorine dioxide treated yeast creams (treated as set forth in Example 1.1) into 400 mL of lignocellulosic hydrolysate. The lignocellulosic hydrolysate was produced as set forth in Example 1.1. Prior to inoculation, the media was sparged with pure $CO_2$ for two minutes to ensure anaerobicity. Cells were allowed to ferment at 30° C., 150 rpm until sugar exhaustion. $CO_2$ production was monitored for the course of the fermentation and samples were taken for dry cell weight and HPLC analysis.

The samples were analyzed for cell mass using dry cell weight (Rice et al. (1980) *Am. Soc. Brew. Chem. J.* 38:142-45, which is incorporated herein by reference). For the fermentability analysis, samples were taken from the bioreactors using a 10 mL syringe. From each sample, cells in 2 mL culture samples were pelleted by centrifugation and the supernatant decanted and filtered through a 0.2 μm syringe filter. Each supernatant sample was diluted with 5 mM sulfuric acid. All dilutions were analyzed for glucose, xylose, xylitol, glycerol, and ethanol content on the Agilent 1100 Series Refractive Index Detector HPLC, while acetic and lactic acid were analyzed concurrently using an Agilent 1200 Series Variable Wavelength Detector HPLC. The column used for separation was the Varian Metacarb 87H Organic Acid column, maintained at 50° C. with a 5 mM sulfuric acid mobile phase at a flow rate of 0.6 mL/min. The unit was equipped with the 1100 Series Auto-sampler and Pumping System and controlled with the Chemstation software.

Figure 5:
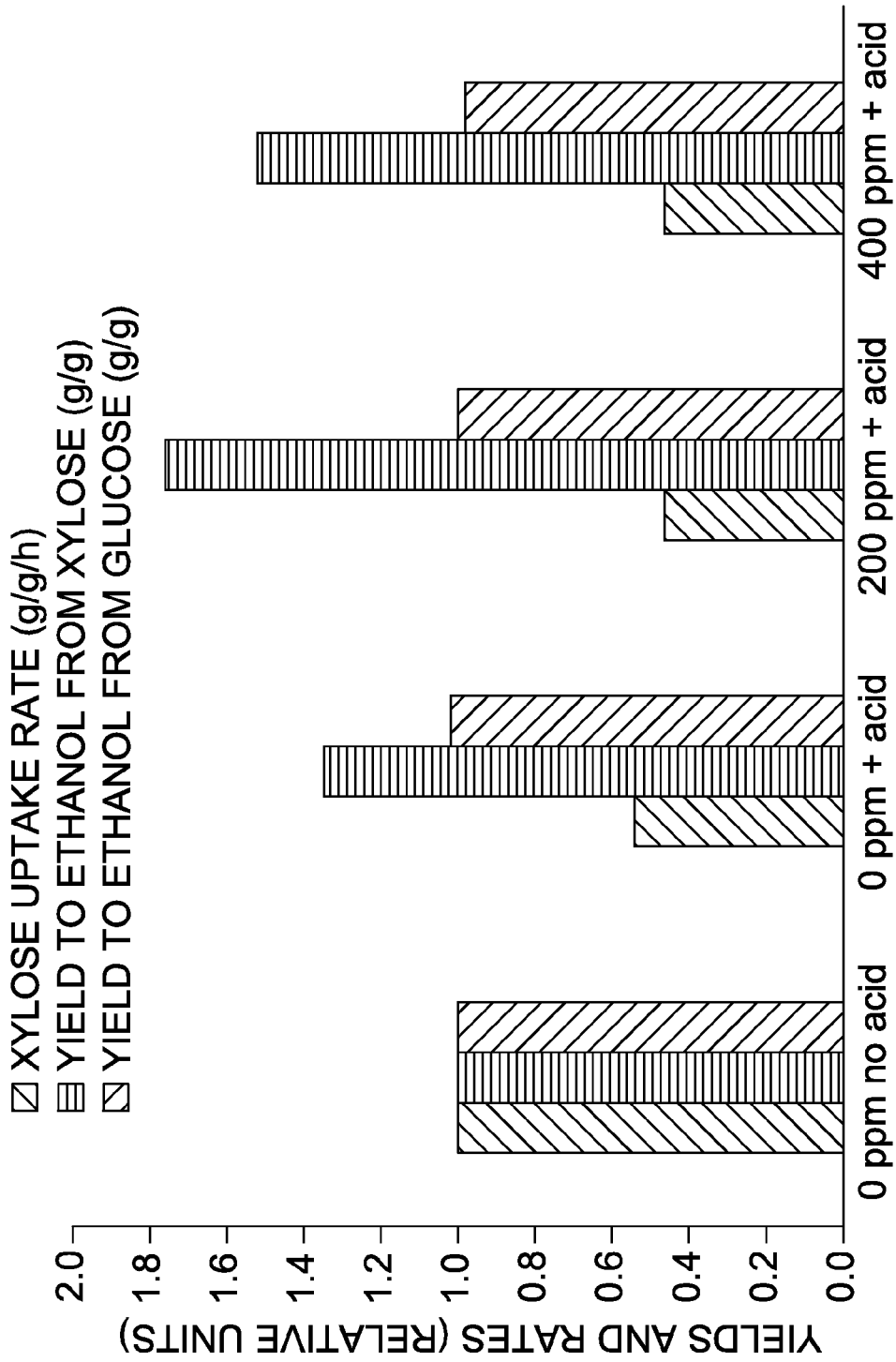
FIG. 5 is a bar graph showing fermentation yields to ethanol from glucose and xylose and xylose uptake rates. Fermentation of lignocellulosic hydrolysate was performed with contaminated yeast cream after treatment with 0, 200 and 500 ppm chlorine dioxide preceded by titration with sulfuric acid to pH 2.

Rates of xylose uptake and yields to ethanol from glucose and xylose for the fermentation of lignocellulosic hydrolysate are shown in FIG. 5. Using equivalent cell concentrations, the xylose consumption rate in the lignocellulosic hydrolysate exhibits a relative decrease with both acid treatment and combination acid-chlorine dioxide treatment. It follows that the rate of xylose consumption would be higher in the untreated control as the contaminating microbes consume xylose. This is further supported by the change observed in ethanol yield from xylose. The decreased rates indicate bacteria are no longer consuming xylose and allow more of this sugar to be converted to ethanol by the fermenting yeast, thus increasing yield. It may also be observed that the decrease in rates, coupled with the increase in yields is greater with the combination acid-chlorine dioxide treatment than with acid treatment alone.

Example 3

Anti-Bacterial Effect of Chlorine Dioxide and pH in Industrial Scale Operations

Hydrolysate from a dilute acid pretreated lignocellulosic feedstock was produced as set forth in U.S. Pat. No. 4,461,648 (incorporated herein by reference). The hydrolysate was fermented to produce ethanol with the yeast strain set forth in co-pending and commonly owned, WO 2009/026706 (incorporated herein by reference).

A volume of 100,000 L whole fermentation broth was separated into a beer fraction and a yeast cream after completion of the fermentation. The yeast cream was concentrated to approximately 170 g dry cell weight/L. Prior to recycle into the next fermentation batch, the yeast cream contaminated with bacteria was treated at 20° C. with acid alone (batch 1) or treated with acid in combination with chlorine dioxide (batch 2). During acid treatment for each of the two batches, the pH of the concentrated yeast cream was lowered to 2.0 using in-line addition of 93% (w/v) sulfuric acid. Chlorine dioxide was generated in concentrated form at a nominal concentration of 2700 ppm using a system commercially available from Pureline, Palatine, Ill. In the combination treatment, the acidity of the yeast cream was first lowered to pH 2.0 (as per Example 1.1) and subsequently treated at a bolus dose of 200 ppm chlorine dioxide with a residence time of approximately 45 seconds. After treatment, the yeast cream was fed back into the fermentation.

Bacterial colonies were enumerated via standard plate count methods. In order to selectively plate bacterial colonies and inhibit yeast growth, tryptic soy agar plates (15 g/L pancreatic digest of casein, 5 g/L enzymatic digest of soybean meal, 5 g/L sodium chloride and 15 g/L agar) with 100 mg/L cycloheximide were used. Samples were serially diluted into sterile saline (0.9% NaCl w/v) prior to plating.

Figure 6:
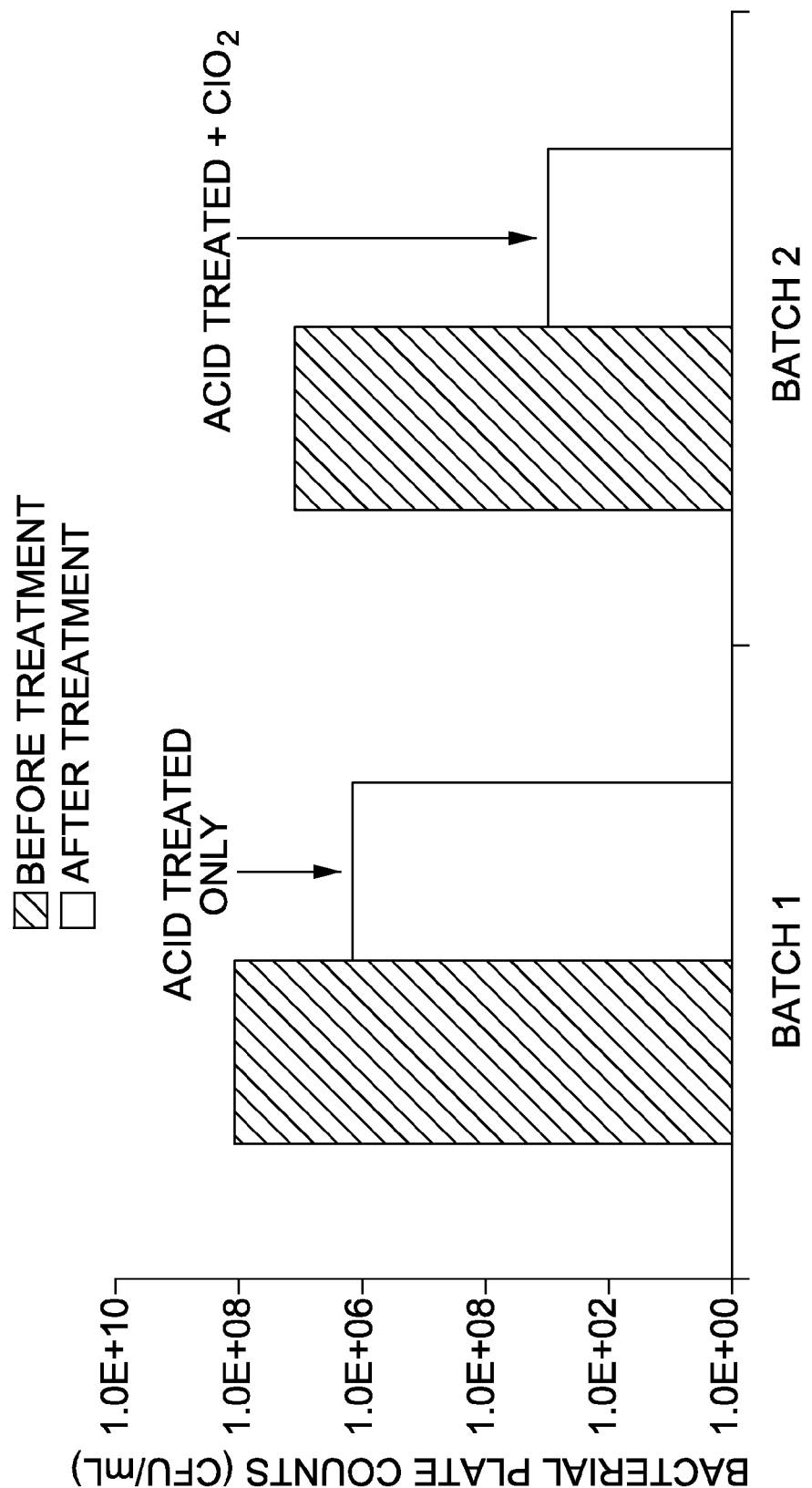
FIG. 6 is a bar graph showing bacterial counts (CFU/mL) of a yeast cream obtained from an industrial fermentation before and after titration with acid to a pH of 2.0 and before and after combined treatment of chlorine dioxide and acid to achieve a pH of 2.0. Filled bars and open bars indicate bacterial counts before treatment and after treatment, respectively.

FIG. 6 illustrates the effectiveness of combined acid treatment and low pH chlorine dioxide use. Lowering the pH through addition of sulfuric acid reduced bacterial contamination counts by $10^2$ CFU/mL, while acid treatment in combination with the addition of chlorine dioxide was able to decrease bacterial contamination counts by $10^4$ CFU/mL.

The present invention has been described with regard to one or more embodiments. However, it will be apparent to persons skilled in the art that a number of variations and modifications can be made without departing from the scope of the invention as defined in the claims.

What is claimed is:

1. A method for producing a fermentation product from a sugar hydrolysate comprising:
   (i) fermenting the sugar hydrolysate in a fermentation system with yeast to produce a fermentation broth comprising a fermentation product;
   (ii) introducing acid and chlorine dioxide to said fermentation system so as to expose any microbial contaminants in said fermentation system at one or more stages to chlorine dioxide at a pH of less than 3.0; and
   (iii) recovering the fermentation product.

2. The method according to claim 1, wherein the sugar hydrolysate comprises at least xylose, glucose or a combination thereof.

3. The method according to claim 2, wherein in the step of fermenting, the fermentation product is ethanol and wherein the yeast is a *Saccharomyces* spp. that converts glucose and xylose to ethanol.

4. The method according to claim 3, wherein the sugar hydrolysate comprises xylose.

5. The method according to claim 1, wherein in the step of introducing, the chlorine dioxide is added at a concentration of between about 0.5 and about 1500 ppm.

6. The method according to claim 5, wherein in the step of introducing, the chlorine dioxide is added at a concentration of between about 75 and about 500 ppm.

7. The method according to claim 1, wherein the sugar hydrolysate is derived from a lignocellulosic feedstock.

8. The method according to claim 7, wherein the sugar hydrolysate is obtained by pretreating the lignocellulosic feedstock with acid or alkali to produce a pretreated feedstock.

9. The method according to claim 1, wherein during said exposing, the pH is greater than about 1, but less than 2.5.

10. The method according to claim 1, wherein during said exposing, the pH is greater than or equal to 1 and less than or equal to 2.5.

11. The method according to claim 1, wherein during said exposing, the acid is added prior to the chlorine dioxide.

12. The method according to claim 1, wherein, in the step of introducing, the yeast in said fermentation system are exposed to chlorine dioxide at a pH of less than 3.0.

13. The method of claim 1, wherein the sugar hydrolysate is a clarified sugar solution.

14. The method of claim 13, wherein the step of introducing acid and chlorine dioxide to said fermentation system comprises
(a) separating the yeast from the fermentation broth to produce a yeast slurry and a fermentation product;
(b) introducing acid and chlorine dioxide to the yeast slurry so as to expose any microbial contaminants and yeast in said yeast slurry to chlorine dioxide at a pH of less than 3.0, thereby producing a chlorine dioxide-treated yeast slurry;
(c) re-introducing at least a portion of the chlorine dioxide-treated yeast slurry back to the step of fermenting.

15. A method for obtaining a fermentation product from a sugar hydrolysate comprising:
(i) removing suspended fiber solids from the sugar hydrolysate to obtain a clarified sugar solution;
(ii) fermenting sugar in the clarified sugar solution in a fermentation reaction using yeast to produce a fermentation broth comprising the fermentation product;
(iii) separating the yeast from the fermentation broth to produce a yeast slurry and a fermentation product;
(iv) introducing acid and chlorine dioxide to the yeast slurry so as to expose any microbial contaminants and yeast in said yeast slurry to chlorine dioxide at a pH of less than 3.0;
(v) re-introducing at least a portion of the chlorine dioxide-treated yeast slurry back to the step of fermenting to maintain the concentration of yeast in the fermentation reaction; and
(vi) recovering the fermentation product.

16. The method according to claim 15, wherein the step of fermenting (step ii) is conducted in one of a series of fermentation reactors and wherein in the step of re-introducing (step v) the chlorine dioxide-treated yeast slurry is re-introduced back to the same or a different fermentation reactor in the series.

17. The method according to claim 15, wherein in the step of introducing, the concentration of the microbial contaminants in the yeast slurry is reduced to at least 100-fold lower than that of the yeast.

18. The method according to claim 15, wherein in the step of introducing, the concentration of microbial contaminants in the yeast slurry is reduced below about $10^3$ CFU/mL.

19. The method according to claim 15, wherein in the step of introducing, the concentration of yeast cells in the yeast slurry is from about 10 g/L to about 300 g/L dry cell weight.

20. The method according to claim 19, wherein in the step of introducing, the concentration of yeast cells in the yeast slurry is from about 20 g/L to about 200 g/L dry cell weight.

21. A method for producing a fermentation product from a sugar hydrolysate comprising:
(i) fermenting the sugar hydrolysate in a fermentation system with yeast to produce a fermentation broth comprising a fermentation product;
(ii) introducing acid and an oxidant to said fermentation system so as to expose any microbial contaminants in said fermentation system at one or more stages to the oxidant at a pH of less than 3.0; and
(iii) recovering the fermentation product.

22. The method of claim 21, wherein the step of introducing comprises continuously introducing the acid and the oxidant to said fermentation system so as to continuously expose the microbial contaminants in said fermentation system to the oxidant.

23. The method of claim 21, wherein the sugar hydrolysate is a clarified sugar solution.

24. The method of claim 23, wherein the step of introducing acid and oxidant to said fermentation system comprises:
(a) separating the yeast from the fermentation broth to produce a yeast slurry and a fermentation product;
(b) introducing acid and oxidant to the yeast slurry so as to expose any microbial contaminants and yeast in said yeast slurry to the oxidant at a pH of less than 3.0, thereby producing an oxidant-treated yeast slurry;
(c) re-introducing at least a portion of the oxidant-treated yeast slurry back to the step of fermenting.

* * * * *